United States Patent
Rudin et al.

(10) Patent No.: US 10,019,795 B2
(45) Date of Patent: Jul. 10, 2018

(54) FOCAL SPOT DE-BLURRING

(71) Applicants: The Research Foundation for the State University of New York, Amherst, NY (US); Toshiba Medical Systems Corporation, Otawara-shi (JP)

(72) Inventors: Stephen Rudin, Buffalo, NY (US); Daniel R. Bednarek, Buffalo, NY (US); Amit Jain, Amherst, NY (US); Joseph Manak, Albany, NY (US)

(73) Assignees: The Research Foundation for the State University of New York, Amherst, NY (US); Toshiba Medical Systems Corporation, Otawara-shi (JP)

( * ) Notice: Subject to any disclaimer, the term of this patent is extended or adjusted under 35 U.S.C. 154(b) by 50 days.

(21) Appl. No.: 15/237,203

(22) Filed: Aug. 15, 2016

(65) Prior Publication Data
US 2018/0047156 A1  Feb. 15, 2018

(51) Int. Cl.
| | |
|---|---|
| *G06T 7/00* | (2017.01) |
| *A61B 6/03* | (2006.01) |
| *A61B 6/00* | (2006.01) |
| *G06T 7/60* | (2017.01) |
| *G06T 3/40* | (2006.01) |

(52) U.S. Cl.
CPC ............ *G06T 7/0012* (2013.01); *A61B 6/032* (2013.01); *A61B 6/5258* (2013.01); *A61B 6/5294* (2013.01); *G06T 3/40* (2013.01); *G06T 7/60* (2013.01); *G06T 2207/10081* (2013.01); *G06T 2207/10116* (2013.01); *G06T 2207/30004* (2013.01)

(58) Field of Classification Search
CPC ......... G06T 3/0056; G06T 3/40; G06T 5/001; G06T 5/003; G06T 5/20; G06T 7/0012; G06T 7/60; A61B 6/5258; A61B 6/5282; A61B 6/5294
See application file for complete search history.

(56) References Cited

U.S. PATENT DOCUMENTS

2016/0019678 A1   1/2016   Cecil ....................... G06T 5/00

FOREIGN PATENT DOCUMENTS

JP   2015-73725 A   4/2015

OTHER PUBLICATIONS

Robert J. Hanisch, et al., "Deconvolution of Hubble Space Telescope Images and Spectra", Deconvolution of Images and Spectra, Second Edition, Jan. 1997, 4 pages (Abstract and Summary only).

(Continued)

*Primary Examiner* — Andrew W Johns
(74) *Attorney, Agent, or Firm* — Oblon, McClelland, Maier & Neustadt, L.L.P.

(57) ABSTRACT

A radiography apparatus includes a radiation source, a radiation detector, and processing circuitry. The processing circuitry is configured to obtain an X-ray image of an object, obtain a focal spot size of a radiation source used to generate the obtained X-ray image, and estimate a magnification of the obtained X-ray image. The processing circuitry is also configured to obtain, using a look-up table and the obtained focal spot size, a deconvolution kernel. The processing circuitry is also configured to generate a corrected X-ray image by performing a deconvolution operation on the obtained X-ray image using the obtained deconvolution kernel and the estimated magnification.

15 Claims, 12 Drawing Sheets

(56) References Cited

OTHER PUBLICATIONS

Amit Jain, et al., "Focal spot measurements using a digital flat panel detector", Proc. Spie. Int. Soc. Opt. Eng., vol. 9033, Mar. 19, 2014, 9 pages.

David S. C. Biggs, et al., "Acceleration of Iterative Image Restoration Algorithms", Applied Optics, vol. 36, No. 8, Mar. 10, 1997, pp. 1766-1775.

240A

Look-up Table (LUT)

| FS | kVp | mAs | Kernel |
|---|---|---|---|
| $FS_1$ | $kVp_1$ | $mAs_1$ | $K_{111}$ |
| $FS_1$ | $kVp_1$ | $mAs_2$ | $K_{112}$ |
| $FS_1$ | $kVp_1$ | $mAs_3$ | $K_{113}$ |
| $FS_1$ | $kVp_2$ | $mAs_1$ | $K_{121}$ |
| $FS_1$ | $kVp_2$ | $mAs_2$ | $K_{122}$ |
| $FS_1$ | $kVp_2$ | $mAs_3$ | $K_{123}$ |
| $FS_1$ | $kVp_3$ | $mAs_1$ | $K_{131}$ |
| $FS_1$ | $kVp_3$ | $mAs_2$ | $K_{132}$ |
| $FS_1$ | $kVp_3$ | $mAs_3$ | $K_{133}$ |
| $FS_2$ | $kVp_1$ | $mAs_1$ | $K_{211}$ |
| $FS_2$ | $kVp_1$ | $mAs_2$ | $K_{212}$ |
| $FS_2$ | $kVp_1$ | $mAs_3$ | $K_{213}$ |
| $FS_2$ | $kVp_2$ | $mAs_1$ | $K_{221}$ |
| $FS_2$ | $kVp_2$ | $mAs_2$ | $K_{222}$ |
| $FS_2$ | $kVp_2$ | $mAs_3$ | $K_{223}$ |
| $FS_2$ | $kVp_3$ | $mAs_1$ | $K_{231}$ |
| $FS_2$ | $kVp_3$ | $mAs_2$ | $K_{232}$ |
| $FS_2$ | $kVp_3$ | $mAs_3$ | $K_{233}$ |
| $FS_3$ | $kVp_1$ | $mAs_1$ | $K_{311}$ |
| $FS_3$ | $kVp_1$ | $mAs_2$ | $K_{312}$ |
| $FS_3$ | $kVp_1$ | $mAs_3$ | $K_{313}$ |
| $FS_3$ | $kVp_2$ | $mAs_1$ | $K_{321}$ |
| $FS_3$ | $kVp_2$ | $mAs_2$ | $K_{322}$ |
| $FS_3$ | $kVp_2$ | $mAs_3$ | $K_{323}$ |
| $FS_3$ | $kVp_3$ | $mAs_1$ | $K_{331}$ |
| $FS_3$ | $kVp_3$ | $mAs_2$ | $K_{332}$ |
| $FS_3$ | $kVp_3$ | $mAs_3$ | $K_{333}$ |

FOCAL SPOT DE-BLURRING

BACKGROUND

Radiography systems and methods are widely used, particularly for medical imaging and diagnosis. Radiography systems generally create two-dimensional projection images through a subject's body. A radiation source, such as an X-ray tube, irradiates the body from one side. A collimator, generally adjacent to the X-ray source, limits the angular extent of the X-ray beam, so that radiation impinging on the body is substantially confined to a cone-beam/fan-beam region (i.e., an X-ray projection volume) defining an image volume of the body. At least one detector on the opposite side of the body receives radiation transmitted through the body substantially in the projection volume. The attenuation of the radiation that has passed through the body is measured by processing electrical signals received from the detector.

Devices used in interventional procedures are becoming increasingly complex, which puts an increasing demand on X-ray image quality. A high resolution is desirable to visualize small details of the image. However, spatial resolution can be limited by the detector pixel size.

Un-sharpness is a loss of spatial resolution in a radiographic image. Geometric un-sharpness is caused by aspects of the geometry of the X-ray beam. Two factors related to geometric un-sharpness are the apparent focal spot size and the ratio between object-imager distance (OID) and source-imager distance (SID).

A focal spot is the point where the electron beam strikes a target within an X-ray tube. Fine focal spot sizes will minimize geometric un-sharpness and therefore, give more detailed images. However, it is often difficult to employ fine focal spot sizes due to the X-ray tube loading necessary in the exposure.

Geometric un-sharpness can be minimized by keeping the ratio SID:OID high. This can be accomplished by keeping the OID to a minimum, i.e. keeping the body portion being X-rayed as close to the detector as possible. Keeping the ratio SID:OID high can also be achieved by increasing the SID beyond a normal usage distance, such as a distance greater than 100-110 cm.

In current systems, the focal spot size can be large and therefore, can degrade the overall resolution. A high resolution detector with a smaller pixel size is more sensitive to the resolution degradation, due to a finite size of focal spots and magnification factors. Tube design limitations and X-ray output limitations are not conducive to using an actual point-size focal spot.

The "background" description provided herein is for the purpose of generally presenting the context of the disclosure. Work of the presently named inventors, to the extent it is described in this background section, as well as aspects of the description which may not otherwise qualify as conventional art at the time of filing, are neither expressly nor implicitly admitted as conventional art against the present disclosure.

BRIEF DESCRIPTION OF THE DRAWINGS

A more complete understanding of the disclosure is provided by reference to the following detailed description when considered in connection with the accompanying drawings, wherein:

FIG. 2 is an exemplary look-up table according to one embodiment;

DETAILED DESCRIPTION

Figure 1:
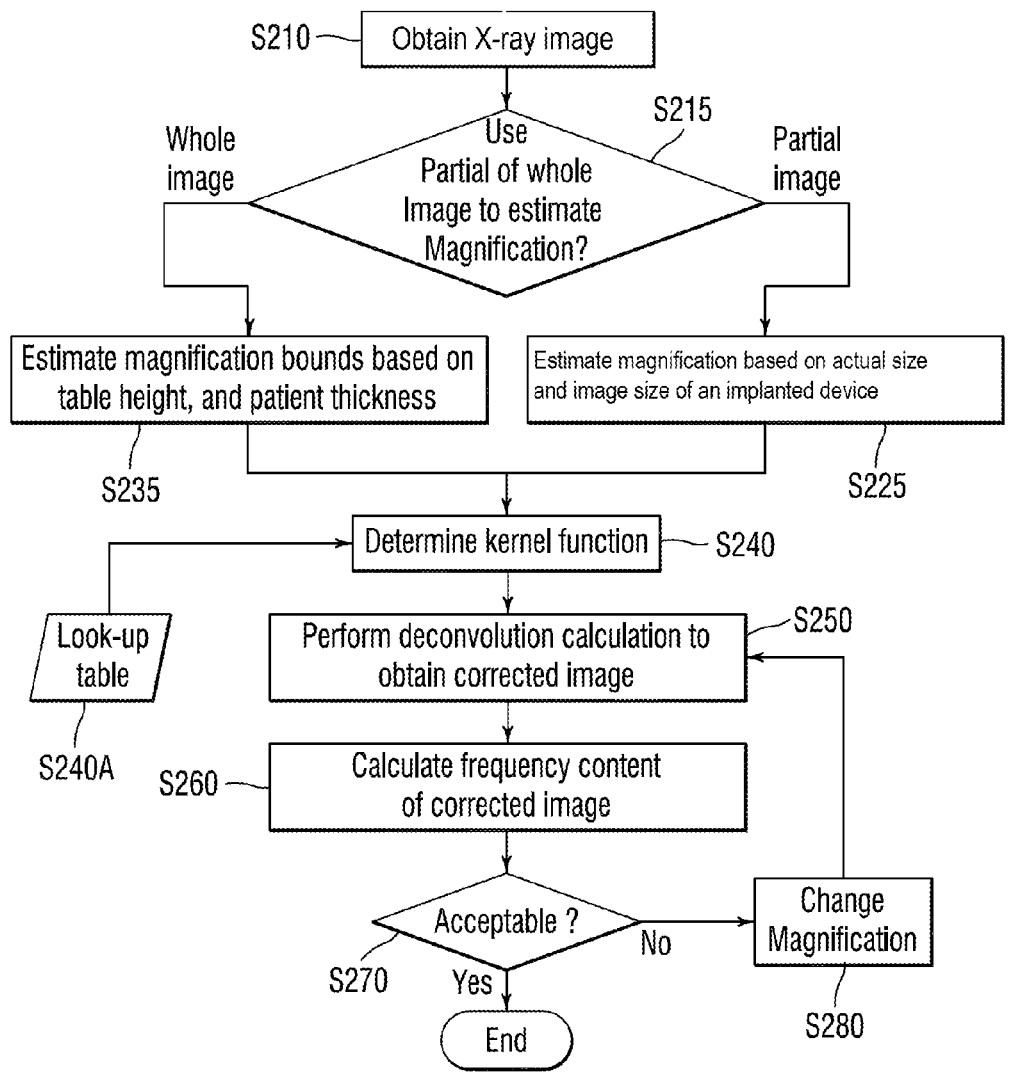
FIG. 1 is an exemplary algorithm for a method of obtaining a corrected image according to one embodiment.

In one embodiment, a radiography apparatus includes processing circuitry. The processing circuitry is configured to obtain an X-ray image of an object, obtain a focal spot size and distribution of a radiation source used to generate the obtained X-ray image, and estimate a magnification of the obtained X-ray image. The processing circuitry is also configured to obtain, using a look-up table and the obtained focal spot size and distribution, a deconvolution kernel. The processing circuitry is also configured to generate a corrected X-ray image by performing a deconvolution operation on the obtained X-ray image using the obtained deconvolution kernel and the estimated magnification.

In another embodiment, a method of obtaining a corrected X-ray image includes obtaining an X-ray image of an object, obtaining a focal spot size and distribution of a radiation source used to generate the obtained X-ray image, and estimating a magnification of the obtained X-ray image. The method also includes obtaining, using a look-up table and the obtained focal spot size and distribution, a deconvolution kernel. The method also includes generating a corrected X-ray image by performing a deconvolution calculation on the obtained X-ray image using the obtained deconvolution kernel and the estimated magnification.

In another embodiment, a radiography apparatus includes a radiation source, a radiation detector, and processing circuitry. The processing circuitry is configured to obtain an X-ray image of an object, obtain a focal spot size and distribution of a radiation source used to generate the obtained X-ray image, and estimate a magnification of the obtained X-ray image. The processing circuitry is also configured to obtain, using a look-up table and the obtained focal spot size and distribution, a deconvolution kernel. The processing circuitry is also configured to generate a corrected X-ray image by performing a deconvolution operation on the obtained X-ray image using the obtained deconvolution kernel and the estimated magnification.

Embodiments described herein include an X-ray system in which a focal spot (FS) size and/or distribution are measured using a pin hole with a high resolution detector. A point spread function (PSF) describes the response of an imaging system to a point source or a point object. In many contexts, the PSF can be thought of as the extended blob in an image that represents an unresolved point object. Hence, the image of a complex object can be seen as a convolution of the true object and its associated PSF.

The relative and absolute values of a measurement can affect various qualities of the radiographic image, as well as the amount of radiation to which a patient is exposed. For example, increasing the patient-to-detector distance alone can improve image contrast by decreasing the amount of scattered radiation that reaches the receptor. However, it will also result in image magnification if the source-to-object distance is not also proportionally increased.

FIG. 1 is an exemplary flowchart for obtaining a corrected image according to one embodiment.

In step S210, an X-ray image is obtained. The obtained X-ray image can be a real-time captured X-ray image or a previously saved X-ray image.

The magnification can be estimated in at least two ways, using either a portion of the obtained image or the entire obtained image. In step S215, it is determined whether the magnification of the image is estimated using a partial image or the entire image of the obtained X-ray image, depending upon the clinical need. An operator can determine settings, depending upon the clinical requirements, i.e., the region viewed by a clinician with higher resolution.

If it is determined in step S215 that a partial image method is to be used to determine the magnification, the estimated magnification is determined in step S225, based on an actual size of an implanted device and an image size of the implanted device. In one example, the implanted device could be a stent. A detailed description of step S225 is given herein with reference to FIGS. 5 and 6.

If it is determined in step S215 that a whole image method is to be used to determine the magnification, the process proceeds to step S235. In step S235, the magnification bounds are estimated based on a source-to-imager distance (SID), a table height, and a patient thickness. The SID is a measurement of the distance between the radiation source and the radiation detector, which is a combined measurement of a source-to-patient distance plus a patient-to-detector distance. A detailed description of step S235 is given herein with reference to FIGS. 7 and 8.

In step S240, a kernel function is selected. In one example, an edge detection kernel or an edge enhancement kernel can be selected. A look-up table (LUT) 240A is used to choose the kernel function.

FIG. 2 is an exemplary LUT 240A used to choose the kernel function. A given X-ray system has certain inherent properties and parameters, including the current milli-ampere-(mA) and peak kilovoltage (kVp) applied at the X-ray source, and the FS size. These parameters can be used as indices into the LUT 240A to determine a resulting kernel function.

The mAs is a product of the tube current and an exposure time, which is a primary controlling factor of radiographic intensity.

The kVp is the maximum voltage applied across an X-ray tube. It determines the kinetic energy of the electrons accelerated in the X-ray tube and the peak energy of the X-ray emission spectrum. The kVp also affects the radiographic contrast indirectly. As the energy of the stream of electrons in the X-ray tube increases, the higher energy X-ray photons created from the higher energy electrons are more likely to penetrate the cells of the body and reach the image receptor. This results in increased radiographic signal magnitude. However, scattered X-rays also contribute to increased radiographic signal magnitude, wherein the higher the kVp of the beam, the more scatter is produced.

The FS size and distribution can vary for each X-ray apparatus. The FS size and distribution depend on the aperture size and distribution of the electron beam source, the wavelengths of the ionizing radiation spectrum, and the focal length. An X-ray apparatus can be configured with different FS sizes and distributions, depending on the desired application. In one embodiment given for illustrative purposes only, small, medium, and large FS sizes are used in the LUT 240A. However, other naming conventions and numbers of FS sizes are contemplated by embodiments described herein.

The variables FS, kVp, and mA are used in the LUT 240A of FIG. 2. However, other variables pertinent to a particular X-ray system can be used. In FIG. 2, three values for each of the variables of FS, kVp, and mA have been used for ease of illustration. However, more or fewer than three values for any one of the variables are contemplated by embodiments described herein.

Figure 3:
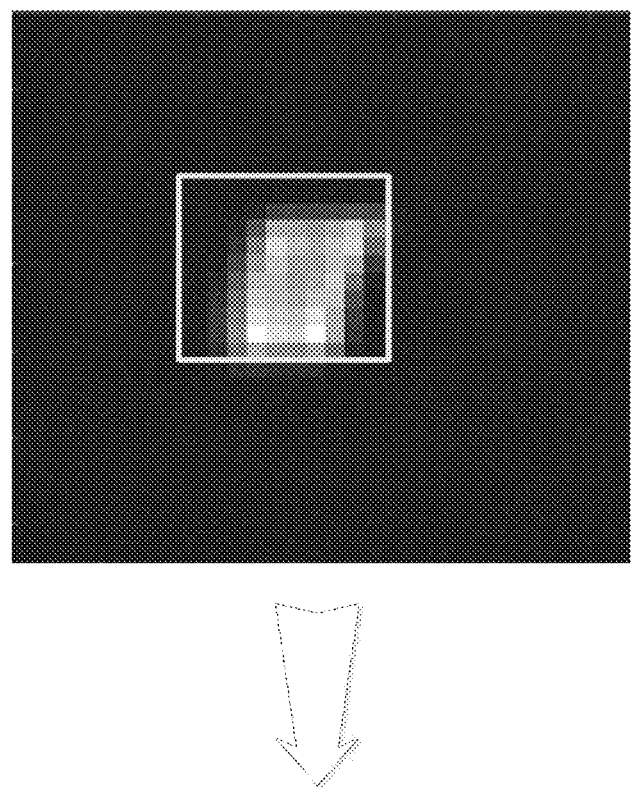
FIG. 3 is an image and an exemplary output kernel according to one embodiment.

FIG. 3 is an image and an exemplary output kernel outputted from the LUT 240A illustrated in FIG. 2. The kernel values outputted from the LUT 240A are pixel values of the image illustrated within the highlighted square in FIG. 3. The highlighted square has been divided, in this example, into a 12×12 grid array of pixels. The table values illustrate the pixel values of the focal spot distribution region within the highlighted square. The kernel is used for subsequent deconvolution calculations, as discussed below. The axis for the kernel can be decided based upon the pixel size of the X-ray detector 103. For example, in a mathematical deconvolution process, the axis/axes information needs to have the detector pixel given in terms of the FS distribution. If the FS distribution is taken using a different detector, such as a higher resolution detector, the axis/axes may need to be modified, based on the pixel size of the imaging detector.

In step S250, a deconvolution calculation is performed to obtain a corrected image. The deconvolution calculation is applied to either the partial image or the whole image. The deconvolution calculation uses the known FS size and/or distribution as well as the estimated magnification from step S225 for a partial image or from step S235 for a whole image. In particular, the magnification is used to scale the focal spot size/distribution kernel, and then the kernel is used in the deconvolution process. Any deconvolution algorithm can be applied after scaling. For example, see Biggs, D. S. C. "Acceleration of Iterative Image Restoration Algorithms." *Applied Optics*. Vol. 36. Number 8,1997, pp. 1766-1775, and Hanisch, R. J., R. L. White, and R. L. Gilliland. "Deconvolution of Hubble Space Telescope Images and Spectra." *Deconvolution of Images and Spectra* (P. A. Jansson, ed.). Boston, Mass.: Academic Press, 1997, pp. 310-356, the contents of each of which is incorporated herein by reference.

A detected image can be viewed as a convolution of the actual image convolved with extraneous blurring, such as the values obtained from the PSF. Therefore, a deconvolution process removes the blur to obtain the original image of the object. Deconvolution is an algorithm-based process used to reverse the effects of convolution on recorded data.

Based on the FS used and the magnification, the image obtained in step S210 is corrected using deconvolution techniques. In one embodiment, multiple iterations are used to obtain improved deconvolution results.

For example, in step S260, the spatial frequency content of the corrected image is calculated. The frequency spectrum can identify outlying data or blur that extends from the desirable frequencies of a target image.

In step S270, it is determined whether the frequency content of the deconvolution calculation is acceptable or not, using predetermined criteria. If the result is acceptable ("YES" in step S270), the process ends.

If the result is not acceptable, i.e., does not satisfy the predetermined criteria ("NO" in step S270), the magnification factor is changed in step S280, and the process returns to step S250 to perform another deconvolution calculation. An amount of change in the magnification factor can be preset or it can depend upon an iterative process converging.

Figure 4:
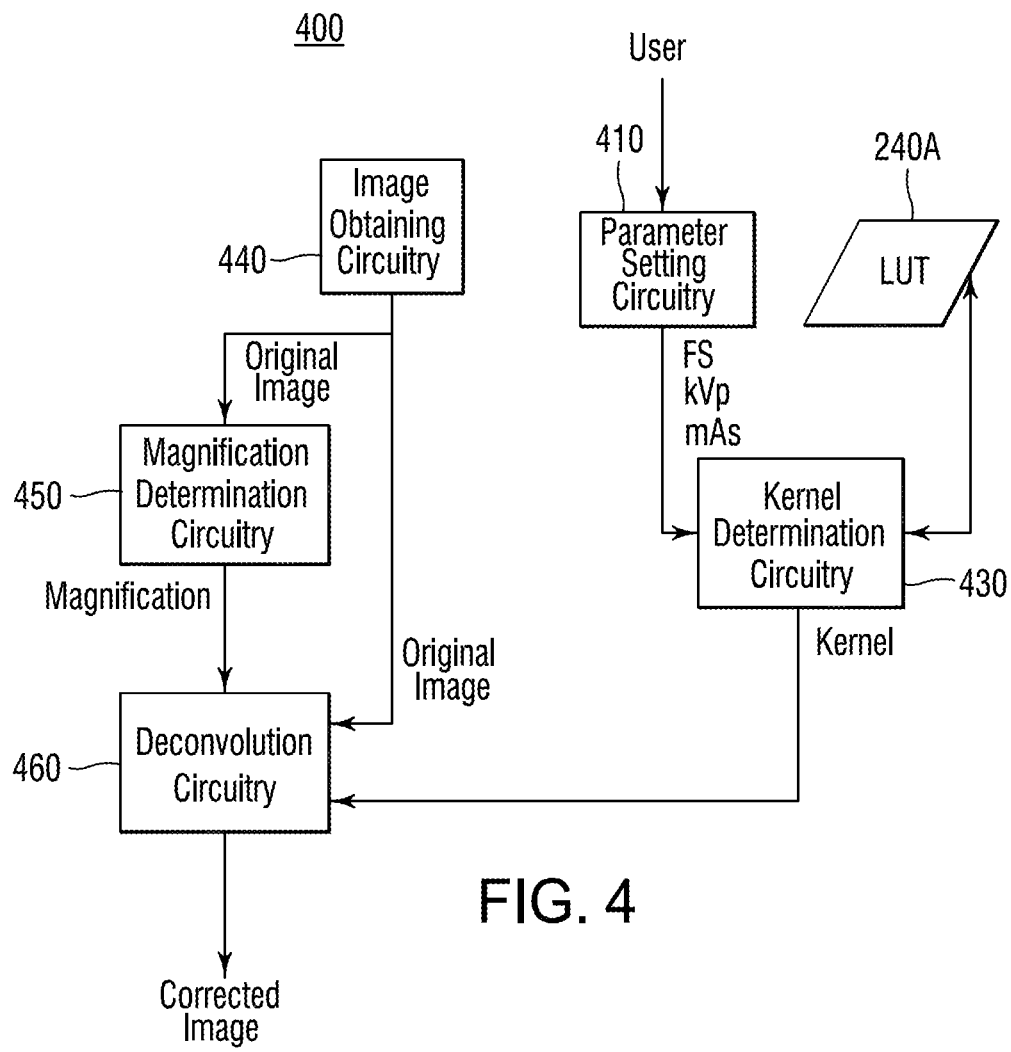
FIG. 4 is a block diagram of exemplary functional circuitry according to one embodiment.

FIG. 4 is a block diagram of the functional elements performed by processing circuitry, such as a CPU, to implement the steps illustrated in FIG. 1. Alternatively, FIG. 4 illustrates dedicated specialized circuitry for implementing the functionality shown in FIG. 1.

A user inputs one or more defined parameters, such as values for the FS, kVp, and/or mA into parameter setting circuitry 410. The kernel selection and implementation circuitry 430 determines the kernel function by accessing the LUT 240A using the defined parameters inputted by the user or otherwise predetermined.

Image obtaining circuitry 440, such as the circuitry of a scanner, is used to obtain data for the X-ray image of step S210. The image data is forwarded to magnification selection circuitry 450, using the estimated magnification from step S225 or the estimated magnification from step S235.

The magnification determined by the magnification determination circuitry 450 and the original image obtained by the image obtaining circuitry 440 are sent to the deconvolution circuitry 460.

The kernel determined by the kernel determination circuitry 430 is also sent to the deconvolution circuitry 460, which performs the deconvolution and outputs a corrected image.

Figure 5:
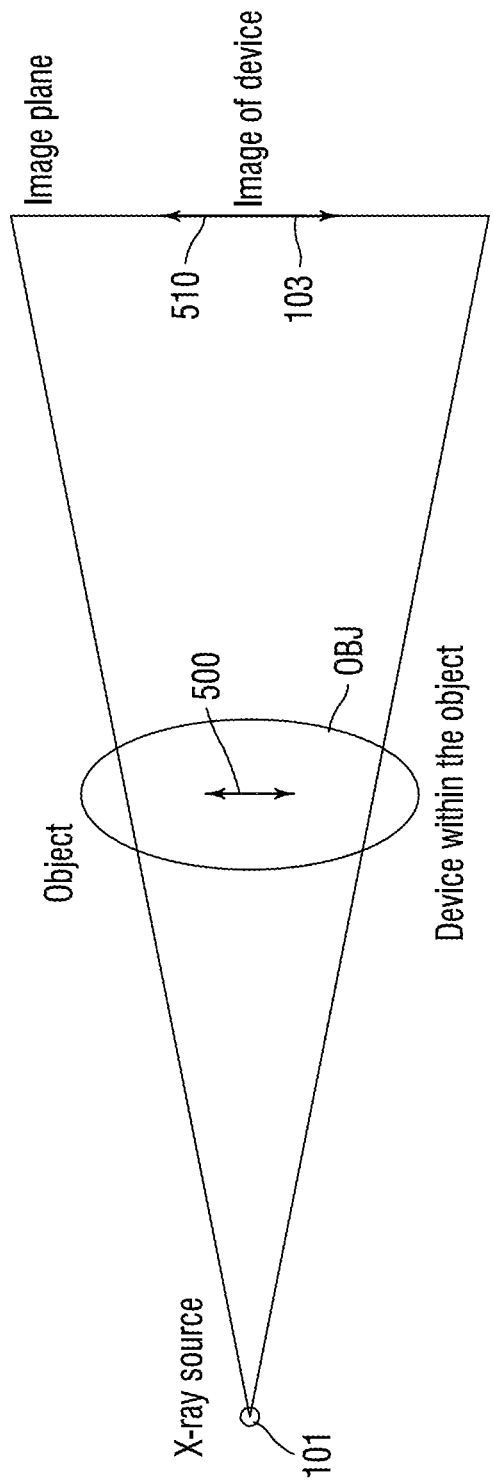
FIG. 5 illustrates an exemplary imaging system according to one embodiment.

FIG. 5 illustrates an exemplary imaging system in which an implanted device within an object or patient is used as a reference to determine the magnification in step S225. An X-ray source 101 provides ionizing radiation through an object OBJ, such as a patient. An image of the penetrating radiation passing through the object OBJ is captured at an X-ray detector 103. The object OBJ contains an implanted device 500, such as a stent. The size and shape of the stent is known. An image 510 is captured at the X-ray detector 103, which includes an image of the implanted device 500. Dimensions of the image of the implanted device 500 can be measured. The ratio of the image dimensions to the actual dimensions of the implanted device 500 is used to determine the magnification of the implanted device 500.

Figure 6:
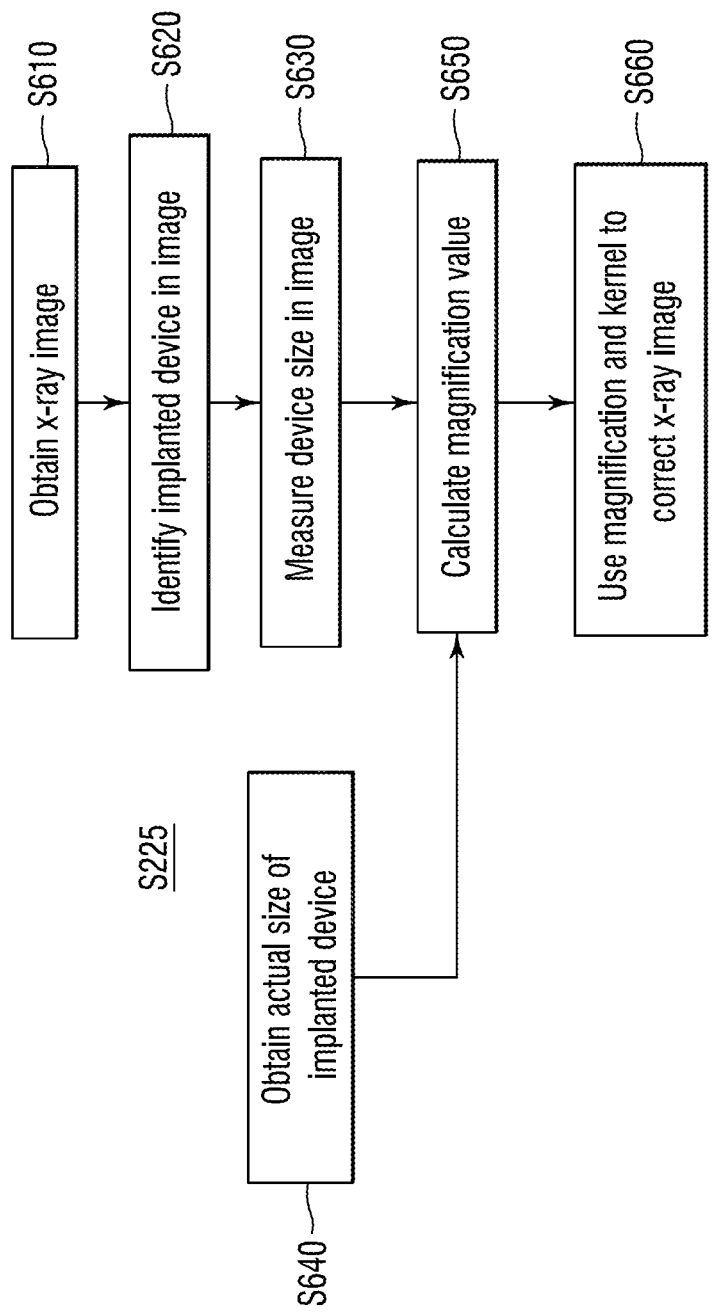
FIG. 6 is a flowchart for a corrected image step using an exemplary imaging system according to one embodiment.

FIG. 6 is a flowchart for the process of step S225 using the exemplary imaging system illustrated in FIG. 5.

In step S225, a partial image is used to estimate the magnification. The partial image can be a region of the whole image, in which small details are present, such as an implanted device.

In step S610, an X-ray image is obtained. The obtained X-ray image can be a real-time captured X-ray image or a previously saved X-ray image.

In step S620, an implanted device is identified in the obtained X-ray image. The implanted device could be a stent or any other device or structure previously implanted in the object or patient.

In step S630, the size, i.e., dimensions of the image of the implanted device are measured. The measured dimensions can be a one- or two-dimensional object, or a three-dimensional object for a series of X-ray images, such as a CT scan.

In step S640, the actual dimensions of the implanted device are obtained. The actual dimensions of the implanted device can be obtained from previous medical records of the patient or from a known serial number of the implanted device.

In step S650, the actual dimensions and the image dimensions of the implanted device are used to calculate the magnification value. The magnification value of the implanted device is a ratio of the image dimensions to the actual dimensions of the implanted device.

In step S660, the magnification ratio and the kernel are used to correct the X-ray image. Subsequent steps for correcting the X-ray image using the magnification ratio and the kernel are described above with reference to steps S240-S280 of FIG. 1.

Figure 7:
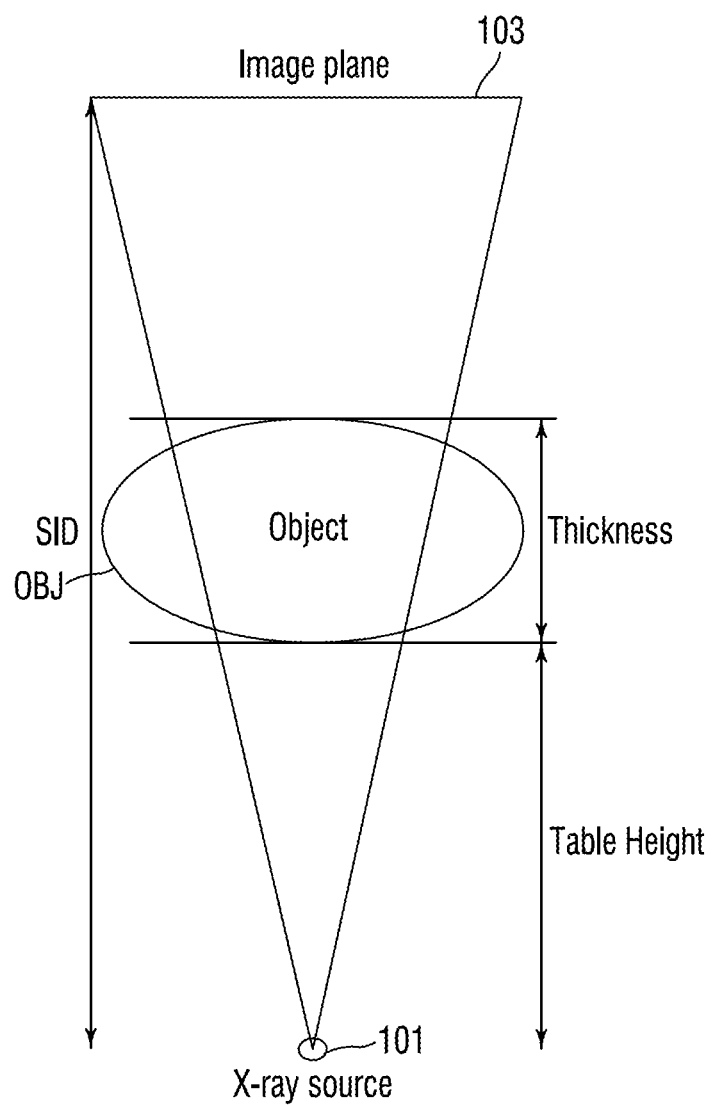
FIG. 7 illustrates an exemplary imaging system according to one embodiment.

FIG. 7 illustrates an exemplary imaging system in which an entire X-ray image is used to determine the magnification in the process of step S235. An X-ray source 101 provides ionizing radiation through an object OBJ, such as a patient. An image of the penetrating radiation passing through the object OBJ is captured at an X-ray detector 103. Dimensions of the SID, a table height, and a thickness of the object OBJ are used to estimate the magnification bounds. The magnification bounds are calculated for a maximum magnification as an upper bound and a minimum magnification as a lower bound. The maximum magnification, max mag is calculated as a ratio of SID over the table height, wherein max mag=SID/table height. The minimum magnification, min mag is calculated as a ratio of SID over a sum of the table height and the object OBJ thickness, wherein min mag=SID/(table height+thickness).

Figure 8:
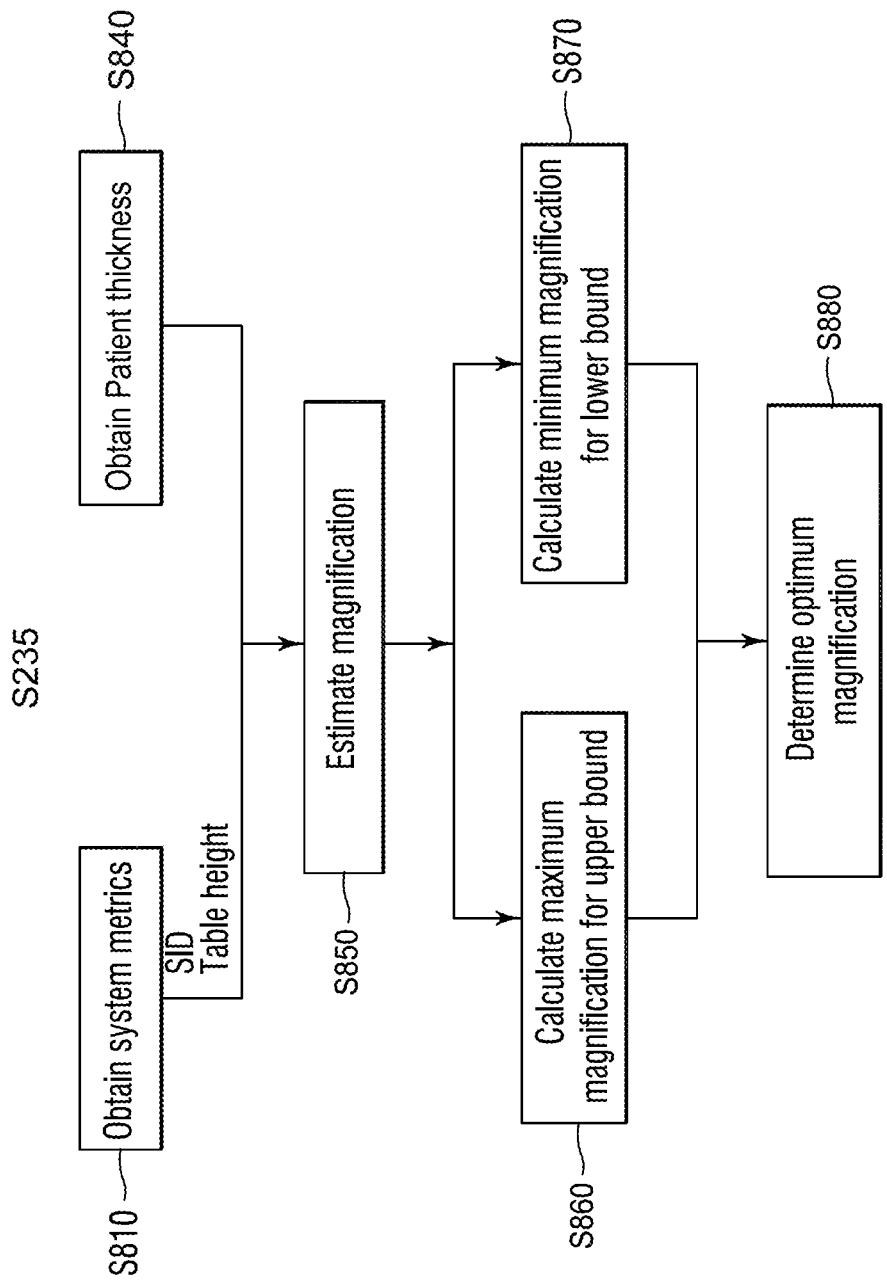
FIG. 8 is a flowchart for a corrected image step using an exemplary imaging system according to one embodiment.

FIG. 8 is a flowchart for the corrected image step S235 using the exemplary imaging system illustrated in FIG. 7. In step S235, the entire image is used to estimate the magnification.

In step S810, metrics for an X-ray system are obtained. Metrics include, but are not limited to, SID and a table height.

In step S840, an object OBJ or patient thickness is obtained. The OBJ thickness can vary greatly, such as the thickness of a young child or the thickness of an obese adult. Therefore, consideration of the thickness of the OBJ can identify an outlying limit to use in estimating the magnification.

In step S850, the magnification bounds of an obtained X-ray image are calculated for a maximum magnification as an upper bound and a minimum magnification as a lower bound.

In step S860, the maximum magnification, "max mag" is calculated as a ratio of SID over the table height, wherein max mag=SID/table height.

In step S870, the minimum magnification, "min mag" is calculated as a ratio of SID over a sum of the table height and the object OBJ thickness, wherein min mag=SID/(table height+OBJ thickness).

In step S880, an optimum magnification between the maximum magnification and the minimum magnification is determined. The optimum magnification could be calculated as an average of the maximum and minimum magnifications. In other embodiments, one or more patient factors can determine, at least in part, the optimum magnification. For example, the region of interest may be located near the front surface of the patient, near the back surface of the patient, or near the mid-region of the patient. The optimum magnification could be determined as, opt mag=SID/(table height+region-of-interest height).

In one embodiment, the optimum magnification can also be determined using a lateral image and obtaining the depth, relative to a thickness of a patient. For example, the thickness measurement can be obtained with a physical caliper. Therefore, the magnification in the lateral is not needed, since the ratio of depth to thickness can be obtained from the lateral image.

In another embodiment, a reference human size can be obtained from medical literature. In an alternative embodiment, the reference human size can be scaled by the known weight, height, and thickness of the patient. The thickness can be approximated from the attenuation of the patient, i.e. knowing the image signal and X-ray tube output.

Figure 9:
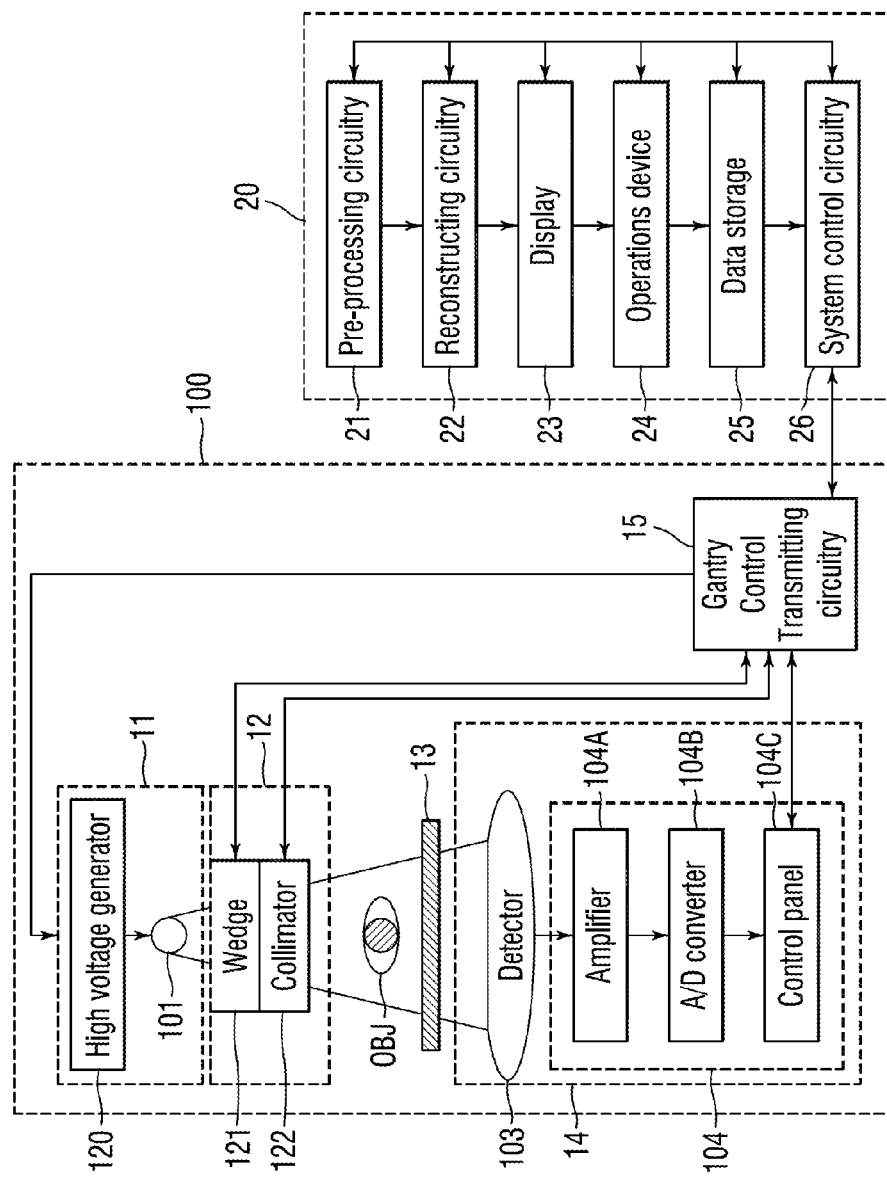
FIG. 9 is a block diagram of an exemplary X-ray apparatus according to one embodiment.

FIG. 9 is a block diagram of an exemplary X-ray apparatus that can be used with embodiments described herein, such as the imaging system illustrated in FIG. 5 and/or the imaging system illustrated in FIG. 7. The X-ray apparatus includes a gantry 100 and a console 20. The gantry 100 includes an X-ray system 11, an optical system 12, a patient table 13, a detection system 14, and a gantry control transmission circuitry 15.

The X-ray system 11 includes a high voltage generator 120 and an X-ray tube 101. The high voltage generator 120 applies a high voltage to the X-ray tube 101 under the control of the gantry control transmission circuitry 15, and supplies a filament current to the X-ray tube 101 under the control of the gantry control transmission circuitry 15. The X-ray tube 101 generates X-rays to be applied to an object OBJ upon receiving a high voltage and a filament current from the high voltage generator 120.

The collimation system 12 includes a filter/attenuator 121 which cuts soft X-rays of X-rays generated from the X-ray tube 101 and adjusts the intensity distribution of the X-rays. A collimator 122 opens and closes in accordance with a field size at the time of a radiograph. The collimation system 12 forms an X-ray beam with an optimized exposure dose and irradiates the object OBJ with X-rays.

The detection system 14 includes the detector 103 and a data acquisition system (DAS) 104. The detector 103 detects the X-rays generated from the X-ray tube 101. The detector 103 is equipped with a plurality of detection elements arrayed two-dimensionally. Each detection element detects the X-rays generated from the X-ray tube 101 and generates an electrical signal (current signal) corresponding to the intensity of the detected X-rays.

The generated electrical signal is supplied to the DAS 104. The DAS 104 includes an amplifier 104A, an A/D converter 104B, and a control panel 104C. The DAS 104 reads out electrical signals via the detector 103 and acquires the readout electrical signals, via the control panel 104C. The gantry control transmission circuitry 15 controls the high voltage generator 120, the attenuator 121, the collimator 122, and the control panel 104 to execute X-ray imaging.

The console 20 includes pre-processing circuitry 21, reconstruction circuitry 22, a display 23, an operation device 24, data storage 25, and system control circuitry 26.

The pre-processing circuitry 21 executes pre-processing, such as logarithmic conversion and sensitivity correction for raw data supplied from the DAS 104, via the gantry control transmission circuitry 15. The data for which the pre-processing has been executed is called projection data.

The reconstruction circuitry 22 reconstructs an image over a reconstruction range associated with the object OBJ and is based on the projection data acquired from the object OBJ.

The display 23 displays the image reconstructed by the reconstruction circuitry 22. The reconstruction circuitry 22 reconstructs a high-resolution image corresponding to an enlargement reconstruction range.

The operation circuitry 24 accepts various types of commands and information inputs from a user, via an input device. An operator can perform, via the operation circuitry 24, an operation to enlarge a partial area of the image displayed by the display 23.

The data storage (memory) 25 stores the raw data and various types of data, such as projection data and images. In addition, the data storage 25 stores control programs for the X-ray apparatus.

The system control circuitry 26 functions as the main circuitry of the X-ray apparatus. The system control circuitry 26 reads out control programs stored in the data storage 25 and loads the programs into the memory. The system control circuitry 26 controls the respective circuitry in the X-ray apparatus in accordance with the loaded control programs.

In one embodiment, a first resolution detector having a first pixel size is used to measure the focal spot, and a second resolution detector having a second pixel size is used to project the corrected X-ray image. The first pixel size is equal to or smaller than the second pixel size.

Figure 10:
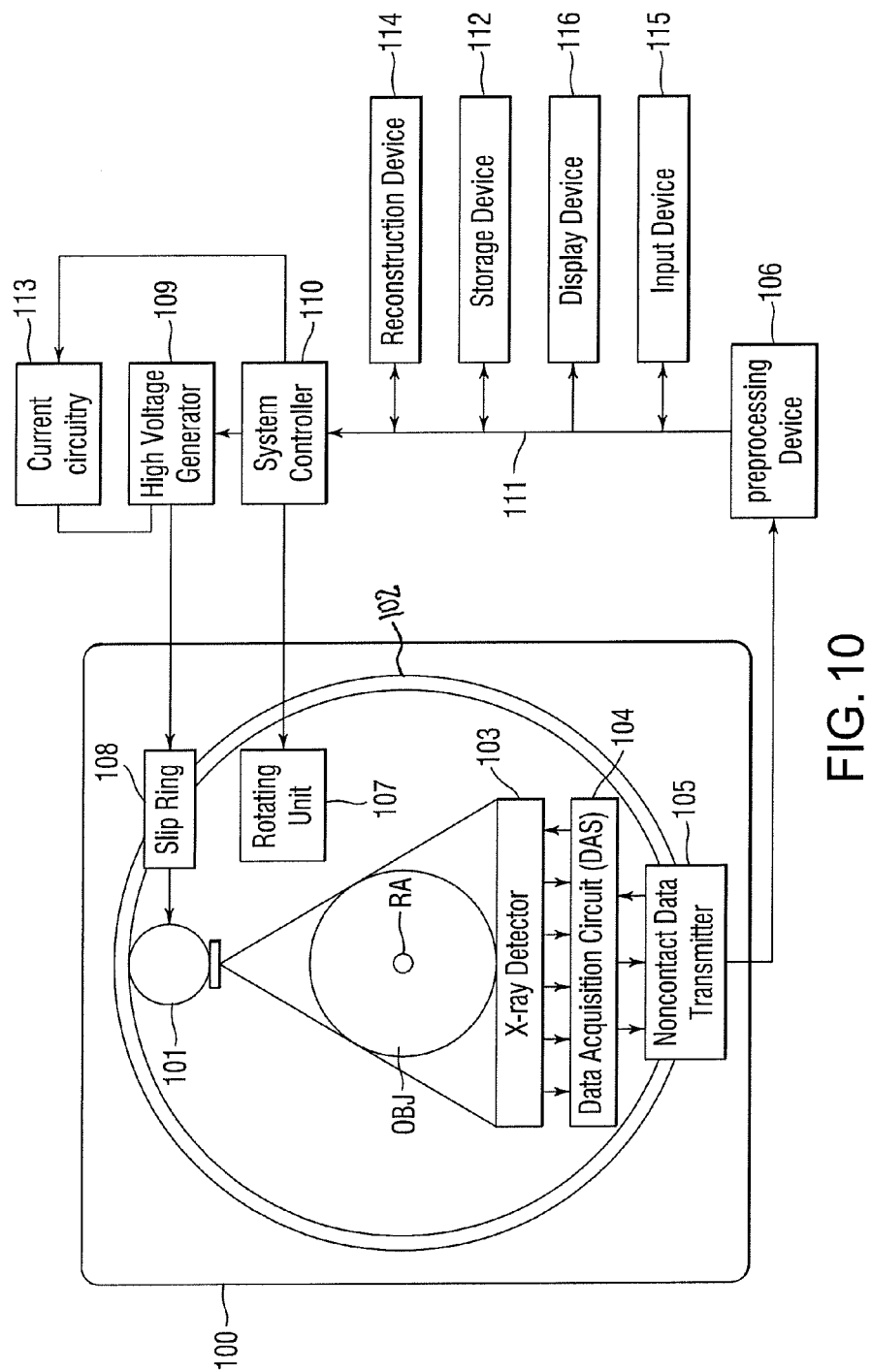
FIG. 10 is a block diagram of an exemplary CT scanner apparatus according to one embodiment.

FIG. 10 is a block diagram of an exemplary CT scanner apparatus that can be used with embodiments described herein, such as the imaging system illustrated in FIG. 5 and/or the imaging system illustrated in FIG. 7. As shown in FIG. 10, a radiography gantry 100 is illustrated from an axial view and further includes an X-ray tube 101, an annular frame 102, and a multi-row or two-dimensional-array-type X-ray detector 103. The X-ray tube 101 and X-ray detector 103 are diametrically mounted across an object OBJ on the annular frame 102, which is rotatably supported around a rotation axis RA. A rotating unit 107 rotates the annular frame 102 at a high speed, such as 0.4 sec/rotation, while the object OBJ is being moved along the axis RA into or out of the illustrated page.

X-ray computed tomography apparatuses include various types of apparatuses. In one example, a rotate/rotate-type apparatus has an X-ray tube and X-ray detector which rotate together around an object to be examined. In a second example, a stationary/rotate-type apparatus has many detection elements which are arrayed in the form of a ring or plane, and only an X-ray tube rotates around an object to be examined. The present disclosures can be applied to either type. With reference to FIG. 10, the rotate/rotate type is illustrated.

The multi-slice X-ray CT apparatus further includes a high voltage generator 109 that generates a tube voltage applied to the X-ray tube 101 through a slip ring 108 so that the X-ray tube 101 generates X-rays. The X-rays are emitted towards the object OBJ, whose cross-sectional area is represented by a circle. The X-ray detector 103 is located at an opposite side from the X-ray tube 101 across the object OBJ for detecting the emitted X-rays that have transmitted through the object OBJ. The X-ray detector 103 further includes individual detector elements or units.

The CT apparatus further includes other devices for processing the detected signals from X-ray detector 103. A data acquisition circuit or a Data Acquisition System (DAS) 104 converts a signal output from the X-ray detector 103 for each channel into a voltage signal, amplifies the signal, and further converts the signal into a digital signal. The X-ray detector 103 and the DAS 104 are configured to handle a predetermined total number of projections per rotation (TPPR). Examples of TPPRs include, but are not limited to 900 TPPR, 900-1800 TPPR, and 900-3600 TPPR.

The above-described data is sent to a pre-processing device 106, which is housed in a console outside the radiography gantry 100 through a non-contact data transmitter 105. The pre-processing device 106 performs certain corrections, such as sensitivity correction on the raw data. A storage device112 stores the resultant data, which is also called projection data at a stage immediately before reconstruction processing. The storage device 112 is connected to a system controller 110 through a data/control bus 111, together with a reconstruction device 114, input device 115, and display device 116. The system controller 110 controls a current regulator 113 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 101 and the X-ray detector 103 are diametrically mounted on the annular frame 102 and are rotated around the object OBJ as the annular frame 102 is rotated about the rotation axis RA. In the fourth-generation geometry system, the detectors are fixedly placed around the patient and an X-ray tube rotates around the patient. In an alternative embodiment, the radiography gantry 100 has multiple detectors arranged on the annular frame 102, which is supported by a C-arm and a stand.

The storage device 112 can store the measurement value representative of the irradiance of the X-rays at the X-ray detector unit 103. Further, the storage device 112 can store a dedicated program for executing the CT image reconstruction methods discussed herein.

The reconstruction device 114 can execute the CT image reconstruction methods discussed herein. Further, reconstruction device 114 can execute pre-reconstruction image processing such as volume rendering processing and image difference processing as needed. The pre-reconstruction processing of the projection data performed by the pre-processing device 106 can include correcting for detector calibrations, detector nonlinearities, polar effects, noise balancing, and material decomposition.

Post-reconstruction processing performed by the reconstruction device 114 can include filtering and smoothing the image, volume rendering processing, and image difference processing as needed. The image reconstruction process can be performed using filtered back projection, iterative image reconstruction methods, or stochastic image reconstruction methods. The reconstruction device 114 can use the storage device 112 to store projection data, reconstructed images, calibration data and parameters, and computer programs, for example.

The reconstruction device 114 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage device 112 can be non-volatile, such as ROM, EPROM, EEPROM or FLASH memory. The storage device 112 can also be volatile, such as static or dynamic RAM. A processor, such as a microcontroller or microprocessor, and storage device 112 can be provided to manage the electronic memory, as well as the interaction between the FPGA or CPLD and the storage device 112.

Alternatively, the CPU in the reconstruction device 114 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor.

In one implementation, the reconstructed images can be displayed on a display device 116. The display device 116 can be an LCD display, CRT display, plasma display, OLED, LED, or any other display known in the art. The storage device 112 can be a hard disk drive, CD-ROM drive, DVD drive, FLASH drive, RAM, ROM or any other electronic storage known in the art.

Figure 12:
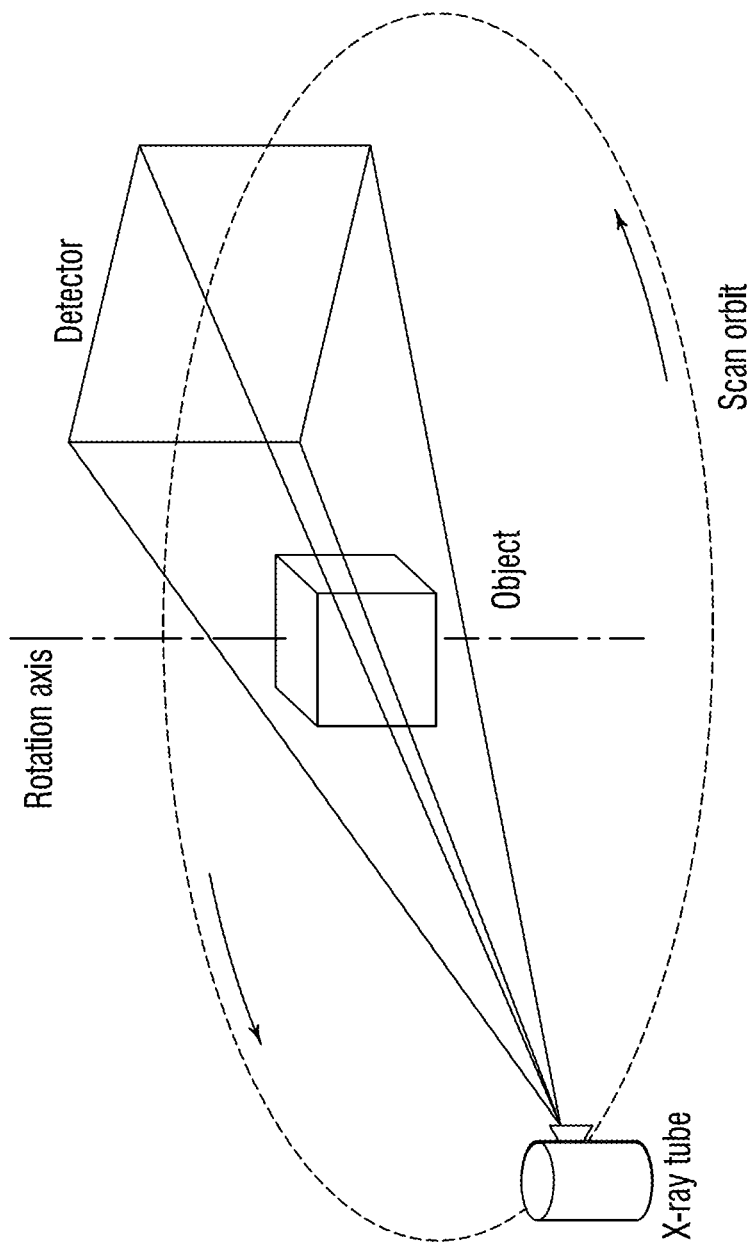
FIG. 12 is a block diagram of an exemplary cone beam CT scanner apparatus according to one embodiment.

FIG. 12 is a block diagram of an exemplary cone beam CT scanner apparatus (also known as a CBCT scanner) that can be used with embodiments described herein, such as the imaging system illustrated in FIG. 5 and/or the imaging system illustrated in FIG. 7. The CBCT scanner rotates about an object, such as a patient. The region of interest is centered in the field of view of the cone beam. A single rotation over the region of interest acquires a volumetric data set, which is collected and reconstructed to produce a digital volume. The digital volume includes three-dimensional voxels of anatomical data, which can be manipulated and visualized, via processing circuitry and associated specialized software.

A hardware description of a computing device 300 according to exemplary embodiments is described with reference to FIG. 11. Computing device 300 includes the system controller 110, the reconstruction device 114, the storage device 112, the display device 116, the input device 115, and/or the preprocessing device 106 illustrated in FIG. 10, either as a combined device or as one or more individual devices. In addition, the gantry control transmitting circuitry 15, the pre-processing circuitry 21, the reconstructing circuitry 22, and the system control circuitry 26 illustrated in FIG. 9 and the functional circuitry illustrated in FIG. 4 are integrated within the computing device 300.

Computing device 300 includes a CPU 301 which performs the processes described above and herein after. The process data and instructions can be stored in memory 302. These processes and instructions can also be stored on a storage medium disk 304 such as a hard disk drive (HDD) or portable storage medium or can be stored remotely. Further, the claimed features are not limited by the form of the computer-readable media on which the instructions of the process are stored. For example, the instructions can be stored on CDs, DVDs, in FLASH memory, RAM, ROM, PROM, EPROM, EEPROM, hard disk or any other information processing device with which the computing device 300 communicates, such as a server or computer.

The claimed features can be provided as a utility application, background daemon, or component of an operating system, or combination thereof, executing in conjunction with CPU 301 and an operating system such as Microsoft Windows 7, UNIX, Solaris, LINUX, Apple MAC-OS and other systems known to those skilled in the art.

The computing device 300 can be realized by various circuitry elements. For example, CPU 301 can be a Xenon or Core processor from Intel of America or an Opteron processor from AMD of America, or can be other processor types that would be recognized by one of ordinary skill in the art. Alternatively, the CPU 301 can be implemented on an FPGA, ASIC, PLD or using discrete logic circuits, as one of ordinary skill in the art would recognize. Further, CPU 301 can be implemented as multiple processors cooperatively working in parallel to perform the instructions of the inventive processes described above and below.

Figure 11:
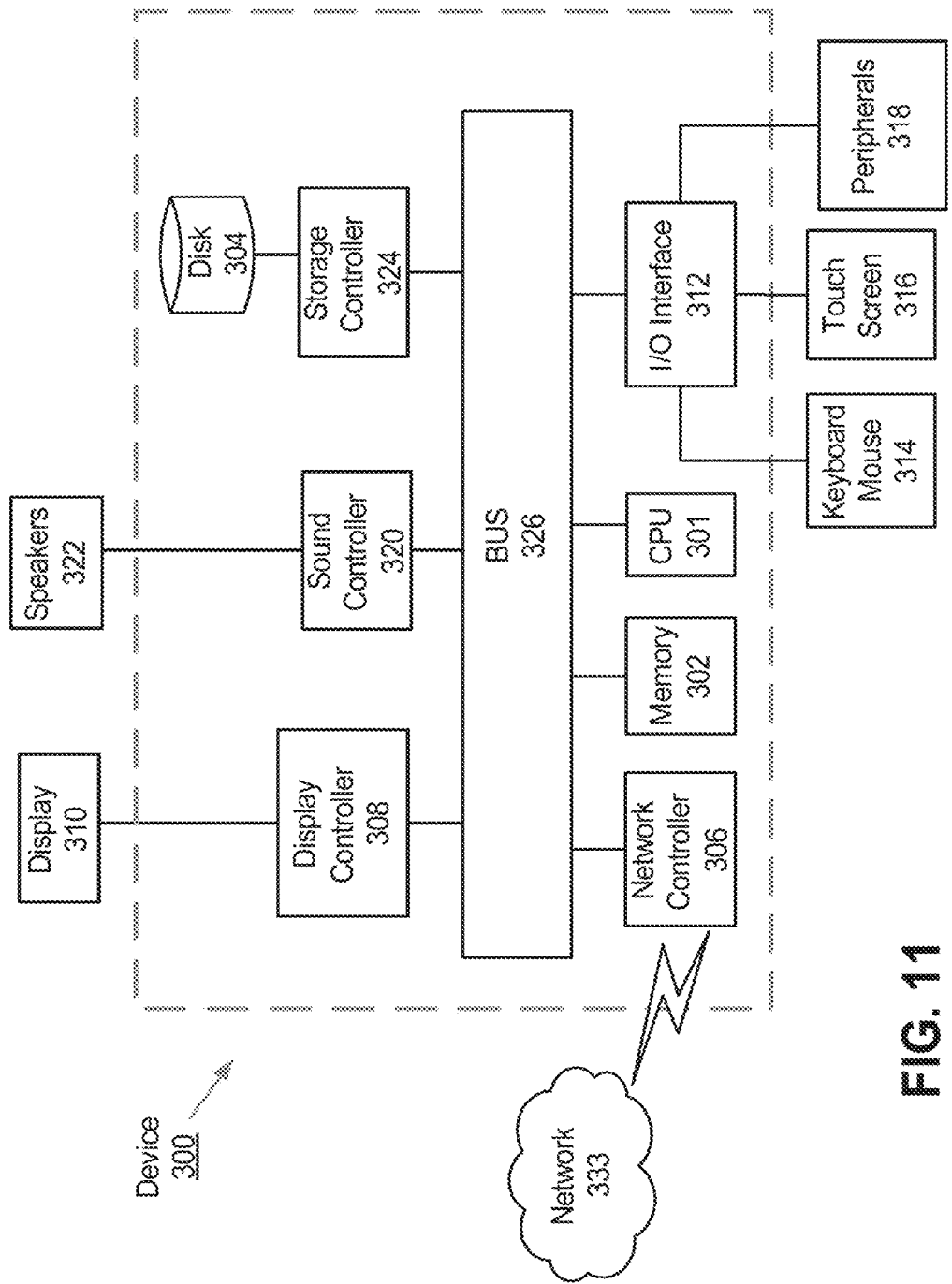
FIG. 11 is a block diagram of a hardware description of a computing device according to one embodiment.

The computing device 300 in FIG. 11 also includes a network controller 306, such as an Intel Ethernet PRO network interface card from Intel Corporation of America, for interfacing with network 333. As can be appreciated, the network 333 can be a public network, such as the Internet, or a private network such as an LAN or WAN network, or any combination thereof and can also include PSTN or ISDN sub-networks. The network 333 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device 300 further includes a display controller 308, such as a NVIDIA GeForce GTX or Quadro graphics adaptor from NVIDIA Corporation of America for interfacing with display 310, such as a Hewlett Packard HPL2445w LCD monitor. A general purpose I/O interface 312 interfaces with a keyboard and/or mouse 314 as well as a touch screen panel 316 on or separate from display 310.

General purpose I/O interface 312 also connects to a variety of peripherals 318 including printers and scanners, such as an OFFICEJET or DESKJET from Hewlett Packard. A sound controller 320 is also provided in the computing device 300, such as SOUNDBLASTER X-FI TITANIUM from Creative, to interface with speakers/microphone 322 thereby providing and/or receiving sounds and/or music.

The general purpose storage controller 324 connects the storage medium disk 304 with communication bus 326, which can be an ISA, EISA, VESA, PCI, or similar, for interconnecting all of the components of the computing device 300. A description of the general features and functionality of the display 310, keyboard and/or mouse 314, as well as the display controller 308, storage controller 324, network controller 306, sound controller 320, and general purpose I/O interface 312 is omitted herein for brevity.

The foregoing discussion discloses and describes merely exemplary embodiments of the present disclosure. As will be understood by those skilled in the art, the present disclosure may be embodied in other specific forms without departing from the spirit or essential characteristics thereof. Accordingly, the present disclosure is intended to be illustrative, but not limiting of the scope of the disclosure, including the claims. The disclosure, including any readily discernible variants of the teachings herein, defines in part, the scope of the foregoing claim terminology such that no inventive subject matter is dedicated to the public.

The invention claimed is:

1. A radiography apparatus, comprising:
 processing circuitry configured to
  obtain an X-ray image of an object,
  obtain a focal spot size and distribution of a radiation source used to generate the obtained X-ray image,
  estimate a magnification of the obtained X-ray image,
  obtain, using a look-up table and the obtained focal spot size and distribution, a deconvolution kernel, and
  generate a corrected X-ray image by performing a deconvolution operation on the obtained X-ray image using the obtained deconvolution kernel and the estimated magnification.

2. The radiography apparatus of claim 1, wherein the processing circuitry is further configured to
 adjust the magnification, and
 perform the deconvolution operation on the corrected X-ray image using the obtained deconvolution kernel and the adjusted magnification.

3. The radiography apparatus of claim 1, further comprising:
 a memory storing the look-up table.

4. The radiography apparatus of claim 1, wherein the processing circuitry is further configured to estimate a magnification range from a source-to-imager distance (SID), an object table height, a lateral image, and an object thickness.

5. The radiography apparatus of claim 4, wherein the processing circuitry is further configured to
 calculate a maximum magnification as a ratio of the SID to the object table height,
 calculate a minimum magnification as a ratio of the SID to a sum of the object table height and the object thickness,
 determine an optimum magnification, between the maximum magnification and the minimum magnification, based on at least one patient factor, and
 set the estimated magnification to be the determined optimum magnification.

6. The radiography apparatus of claim 1, wherein the processing circuitry is further configured to estimate the magnification from an image size of an implanted device within the obtained X-ray image and from an actual known size of the implanted device.

7. The radiography apparatus of claim 6, wherein the processing circuitry is further configured to estimate the magnification as a ratio of the image size to the actual known size of the implanted device.

8. The radiography apparatus of claim 1, wherein the look-up table is indexed by at least one of the available focal spots, a tube current, and a tube voltage.

9. A method of obtaining a corrected X-ray image, comprising:
 obtaining an X-ray image of an object;
 obtaining a focal spot size and distribution of a radiation source used to generate the obtained X-ray image;
 estimating a magnification of the obtained X-ray image;
 obtaining, using a look-up table and the obtained focal spot size and distribution, a deconvolution kernel; and
 generating a corrected X-ray image by performing a deconvolution calculation on the obtained X-ray image using the obtained deconvolution kernel and the estimated magnification.

10. The method of claim 9, wherein the estimating step further comprises:
 estimating the magnification of the obtained X-ray image from a source-to-imager distance (SID), an object table height, and an object thickness.

11. The method of claim 10, wherein the estimating step further comprises:
 calculating a maximum magnification as a ratio of the SID to the object table height,
 calculating a minimum magnification as a ratio of the SID to a sum of the object table height and the object thickness,
 determining an optimum magnification, between the maximum magnification and the minimum magnification, based on at least one patient factor, and
 setting the estimated magnification to be the determined optimum magnification.

12. The method of claim 9, wherein the estimating step further comprises:

estimating the magnification from an image size of an implanted device within the obtained X-ray image and from an actual known size of the implanted device.

13. The method of claim 12, wherein the estimating step further comprises:
estimating the magnification as a ratio of the image size to the actual known size of the implanted device.

14. The method of claim 9, wherein the look-up table is indexed by at least one of the focal spots, a tube current, and a tube voltage.

15. A radiography apparatus, comprising:
a radiation source;
a radiation detector; and
processing circuitry configured to
  obtain an X-ray image of an object,
  obtain a focal spot size and distribution of a radiation source used to generate the obtained X-ray image,
  estimate a magnification of the obtained X-ray image,
  obtain, using a look-up table and the obtained focal spot size and distribution, a deconvolution kernel, and
  generate a corrected X-ray image by performing a deconvolution operation on the obtained X-ray image using the obtained deconvolution kernel and the estimated magnification.

* * * * *